United States Patent [19]
Johnson et al.

[11] Patent Number: 5,871,765
[45] Date of Patent: Feb. 16, 1999

[54] NON-AQUEOUS CONTROLLED RELEASE PEST AND AIR CARE GEL COMPOSITION

[75] Inventors: Richard L. Johnson; David S. Morrison, both of The Woodlands, Tex.

[73] Assignee: Pennzoil Products Company, Houston, Tex.

[21] Appl. No.: 802,775

[22] Filed: Feb. 21, 1997

Related U.S. Application Data

[63] Continuation-in-part of Ser. No. 609,079, Feb. 29, 1996.

[51] Int. Cl.$^6$ .......................... A01N 25/04; A01N 25/10; A61K 9/10; A61K 47/32
[52] U.S. Cl. .................. 424/409; 424/486; 424/DIG. 5; 424/DIG. 10; 514/944; 514/919; 523/122
[58] Field of Search .................................. 424/409, 486, 424/DIG. 5, DIG. 10; 514/944, 919; 523/122; 44/275; 252/315.1

[56] References Cited

U.S. PATENT DOCUMENTS

| | | |
|---|---|---|
| 3,857,805 | 12/1974 | Prickril . |
| 4,369,284 | 1/1983 | Chen . |
| 4,469,613 | 9/1984 | Muteanu et al. . |
| 4,473,582 | 9/1984 | Greene . |
| 4,812,309 | 3/1989 | Ong . |
| 4,906,488 | 3/1990 | Pera . |
| 4,954,332 | 9/1990 | Bissett et al. . |
| 5,132,355 | 7/1992 | Nahlovsky . |
| 5,150,722 | 9/1992 | Rutherford . |
| 5,208,038 | 5/1993 | Gressani et al. . |
| 5,221,534 | 6/1993 | DesLauriers et al. . |
| 5,227,406 | 7/1993 | Beldock et al. . |
| 5,316,744 | 5/1994 | Haehn . |
| 5,578,089 | 11/1996 | Elsamaloty . |

FOREIGN PATENT DOCUMENTS

| | | |
|---|---|---|
| 0 244 389 | 11/1986 | European Pat. Off. . |
| 5-345011 | 12/1993 | Japan . |
| WO88/00603 | 1/1988 | WIPO . |
| WO96/34077 | 10/1996 | WIPO . |

Primary Examiner—Edward J. Webman
Attorney, Agent, or Firm—McDermott, Will & Emery

[57] ABSTRACT

Controlled release non-aqueous air care gels comprising from about 1 to about 50 percent on a weight basis of diblock, triblock, multiblock and/or radial block copolymers based on synthetic thermoplastic rubbers. The ratio of the diblock to triblock, multiblock and/or radial block copolymers can be varied from about 0 percent to about 100 percent in either direction. The material to be gelled is a hydrocarbon, one or more hydrocarbon-soluble substances, or mixtures thereof, which based on its physical properties plays an important role in setting the controlled release rate. The composition of the hydrocarbon can vary in carbon length from about C-5 to about C-30 and can vary in vapor pressure up to about 600 mm Hg at 20° C. The hydrocarbon range on a weight basis is from about 20 to about 95 percent of the total weight of the gelled composition. The controlled release agent or active agent is one or more air care active substances, such as fragrances, deodorizers, masking agents, pest repellents or pesticides, and may comprise from about 0.1 to about 30 weight percent of the gel.

6 Claims, 2 Drawing Sheets

NON-AQUEOUS CONTROLLED RELEASE PEST AND AIR CARE GEL COMPOSITION

CROSS-REFERENCE TO RELATED APPLICATIONS

This application is a Continuation-in-Part of U.S. application Ser. No. 08/609,079, filed Feb. 29, 1996.

FIELD OF THE INVENTION

The invention relates to controlled release polymer gel air care products, such as air fresheners, and the like. More particularly the invention relates to air care products employing non-aqueous, controlled release polymer gels, and more particularly heterophase, thermally reversible hydrocarbon gels which are suitable for use in the controlled release of one or more air care active substances, or pesticidal substances.

The air care product of the invention employs a hydrocarbon gel which contains block copolymer blends, the copolymers being preferably derived from styrene-rubber block units.

BACKGROUND OF THE INVENTION

Controlled release agents have been used in the art in a variety of applications, including the release of pheromones, insect repellents, animal repellents and pharmaceuticals.

For example, U.S. Pat. No. 4,469,613 discloses a detergent bar to release insect repellents which contain poly(ε-caprolactone) homopolymers and other polymers (e.g. polyethylene or polypropylene). U.S. Pat. No. 5,150,722 discloses a low density polyethylene/high density polyethylene copolymer for use in controlled release. Controlled release in the system described therein is affected by the use of a layered structure, with a core containing the agent to be released and a "burst layer" which confines the active substance from being prematurely released.

U.S. Pat. No. 5,316,744 discloses porous particles for controlled release of an active substance. The particles are blocked by use of a cross-linked hydrogel polymer, the blocking agent being sensitive to its physical environment.

Japanese Patent Publication No. 05 345 011 discloses hydrogenated block copolymers of aromatic vinyl compounds as carriers for fragrances, such as room deodorizers.

U.S. Pat. No. 5,221,534 discloses gels comprising a mineral oil and blends of copolymers and including health and beauty aid components.

PCT Patent Application No. WO88/00603 of Francis et al. describes block copolymer compositions which are described as gels or gelloid liquid extended polymer compositions which comprise an intimate mixture of a block copolymer containing relatively hard blocks and relatively elastomeric blocks. A suitable block copolymer is Kraton 1651, a triblock copolymer. The copolymer additionally contains at least 500 parts by weight of extender liquid per 100 parts of the block copolymer, the liquid being present to extend and soften the elastomeric blocks of the block copolymer.

European Patent Application No. 224389 of Gamarra et al. discloses styrene-diene block copolymer compositions and in particular a mixture of triblock copolymers and a hydrocarbon oil. These compositions are useful as sealing materials.

U.S. Pat. No. 4,369,284 describes a transparent gel prepared from triblock copolymers and oils useful as molded products. The triblock copolymers used therein receive specific styrene end blocks to ethylene and butylene center blocks. The end block to center block ratio is given as being between 31:69 and 40:60.

The present invention provides an improved controlled release air care product using unique vehicle systems.

SUMMARY OF THE INVENTION

It is accordingly one object of this invention to provide heterophase, thermally reversible hydrocarbon gel compositions that have advantageous properties when used as a vehicle to solubilize or suspend an air care active substance and effect the controlled-release of said active substance.

A further object of the invention is to provide hydrocarbon gel compositions formed with certain diblock, triblock, radial block and/or multiblock copolymers which have advantageous properties when used as a non-aqueous, controlled release polymer gel for air care active substances.

It is a further object of the invention to provide methods for making controlled release hydrocarbon polymer gel fragrance dispensers, deodorizers, pest repellents, pesticides, and the like, and articles of manufacture employing same.

Other objects and advantages of the present invention will become apparent as the description of the invention proceeds.

In satisfaction of the foregoing objects and advantages, the present invention provides in one embodiment, a non-aqueous, controlled release air care gel composition comprising:

(a) from about 20 to about 95 weight percent of a hydrocarbon, and optionally one or more hydrocarbon-soluble substances;

(b) from about 1 to about 50 weight percent of a diblock, triblock, radial block and/or multiblock copolymers, or blends thereof comprising from about 0 to about 100 weight percent of one or more diblock copolymers and from about 100 to about 0 weight percent of one or more triblock, radial block and/or multiblock copolymer; and (c) from about 0.1 to about 30 weight percent of one or more air care active substances.

The hydrocarbon used in the composition preferably has a vapor pressure up to about 600 mm Hg at 20° C.

The invention further provides methods of making articles of manufacture that are controlled-release active substance dispensers, and methods of using the polymer hydrocarbon gels in these articles.

BRIEF DESCRIPTION OF THE DRAWING

Reference is now made to the drawing accompanying the application wherein.

DETAILED DESCRIPTION OF THE INVENTION

Figure 1:
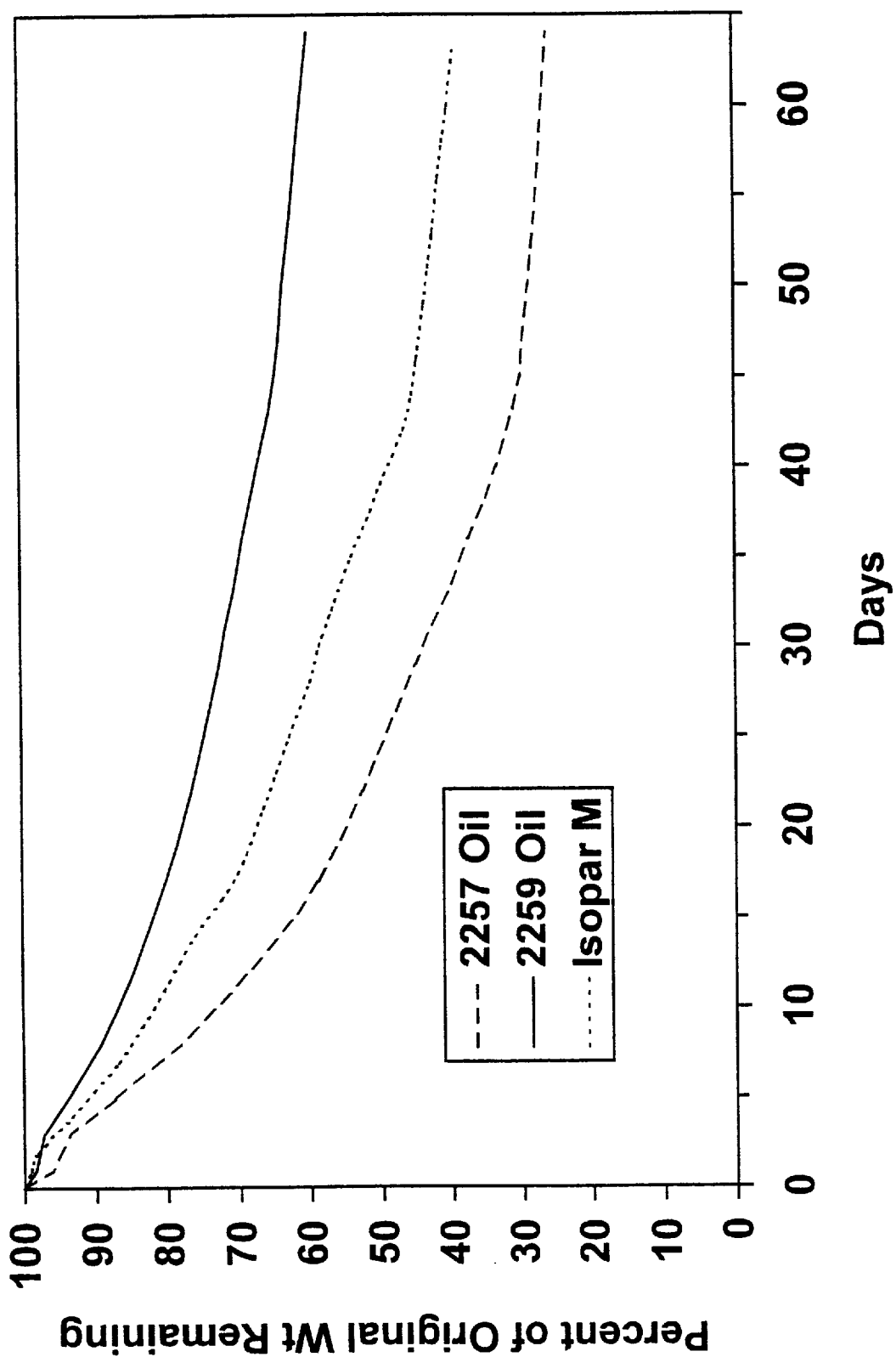
FIG. 1 depicts a comparison of fragrance release over time for air care gels comprising different hydrocarbons.

The present invention is directed to new non-aqueous, controlled release vehicles for the timed release of air care active substances. By the term "air care" is meant substances which are active to affect the air in any manner, which term includes fragrances, deodorizers, masking agents, pest repellents, pesticides, and the like. The controlled release vehicles are hydrocarbon-containing, block copolymer gels.

The products of the invention are useful for the controlled release of fragrant air fresheners, air deodorizers, pesticides, pest repellents and the like such as those employed in the home (e.g., in rooms, closets, garages, workshops, storage areas and cabinets), office, vehicle (e.g., car, truck, van, train, aircraft, watercraft, etc.) and industrial and institutional settings, including public restrooms, warehouses, factories, restaurants and stores.

The non-aqueous, controlled release air care gel compositions of the invention comprise a hydrocarbon, optionally comprising one or more hydrocarbon-soluble substances, one or more diblock copolymers, one or more triblock, radial block and/or multiblock copolymers, or a mixture thereof, and one or more air care active substances.

The invention may accordingly be described as a controlled release air care gel comprising:

(a) from about 20 to about 95 weight percent of a hydrocarbon, optionally containing one or more hydrocarbon-soluble substances, or mixtures thereof;

(b) from about 1 to about 50 weight percent of a diblock, triblock, radial block and/or multiblock copolymers, or a blend thereof comprising from about 0 to about 100 weight percent of one or more diblock copolymer and from about 100 to about 0 weight percent of one or more triblock, radial block and/or multiblock copolymer; and (c) from about 0.1 to about 30 weight percent of one or more air care active substance, such as fragrances or mixtures of fragrances, one or more essential oils, and/or a deodorizer or mixture of deodorizers, where the deodorizers may or may not be fragranced themselves, and/or masking agents, pest repellents, pesticides, etc., as the active ingredients().

In a preferred composition of the invention, the copolymers or blends thereof comprise from about 0.1 to about 25 weight percent, preferably from about 0.1 to about 10 weight percent, of one or more diblock copolymers and from about 70 to about 99.9 weight percent of one or more triblock, radial block and/or multiblock copolymers.

When formed into gels, the copolymers or blends thereof comprise from about 1 to about 50 weight percent of the total weight of the composition. Preferably the total weight of polymer contained in the hydrocarbon will range from about 1 to about 30 weight percent, preferably 5 to 20 weight percent, more preferably about 7 to 18 weight percent, though this preference may change depending upon the particulars of the application desired, as will be apparent to one skilled in the art.

Each of the diblock, triblock, radial block and/or multiblock copolymers used in the invention contains at least two thermodynamically incompatible segments. By the expression thermodynamically incompatible with respect to the polymers, it is meant that the polymer contains at least two incompatible segments, for example, at least one hard and one soft segment. In general, in a triblock polymer, the ratio of segments is one hard, one soft, one hard or an A-B-A copolymer. Diblock copolymers, on the other hand, are of the A-B type and sequential with respect to hard and soft segments. The multiblock and radial block copolymers can contain any combination of hard and soft segments, provided that there are both hard and soft characteristics. These copolymers are fully disclosed in U.S. Pat. No. 5,221,534, the disclosure of which is incorporated herein by reference.

Commercially available thermoplastic rubber type polymers which are especially useful in forming the compositions of the present invention are sold under the trademark Kraton® by Shell Chemical Company. The Kraton® rubber polymers are described as elastomers which have an unusual combination of high strength and low viscosity and a unique molecular structure of linear diblock, triblock and radial copolymers. Each molecule of the Kraton® rubber is said to consist of block segments of styrene monomer units and rubber monomer and/or comonomer units. Each block segment may consist of 100 or more monomer or comonomer units. The most common structure for the triblock copolymer is the above-mentioned linear ABA block type; styrene-butadiene-styrene (SBS) and styrene-isoprene-styrene (SIS), which is the Kraton® D rubber series.

A second polymer of this general type is the Kraton® G series. This copolymer comprises a styrene-ethylenebutylene-styrene type (S-EB-S) structure. The Kraton® G series is preferred in the practice of the invention, as the copolymers of this series are hydrogenated and thus more thermally stable; that is, decomposition is less likely to occur during blending of the G series polymers with the hydrocarbon or hydrocarbon mixture (the D series polymers having unsaturation within the rubber block).

The Kraton® G rubbers are indicated as being compatible with paraffinic and naphthenic oils and the triblock copolymers are reported as taking up more than 20 times their weight in oil to make a product which can vary in consistency from a "Jello®" to a strong elastic rubbery material depending on the grade and concentration of the rubber. The ABA structure of the Kraton® rubber molecule has polystyrene endblocks and elastomeric midblocks.

A preferred triblock polymer is a triblock polymer of the Kraton® G type, in particular Kraton® G-1650. Kraton® G-1650 is an SEBS triblock copolymer which has a specific gravity of about 0.91, and is said to have a tensile strength of about 500 psi as measured by ASTM method D-412-tensile jaw tester separation speed 10 in/min. The styrene to rubber content of Kraton® G-1650 is said by the manufacturer to be about 29:71, and the Brookfield viscosity is about 8000 (toluene solution, cps at 77° F., 25% w). The Shore A hardness is about 75.

The diblock polymers include the AB type such as styrene-ethylenepropylene (S-EP) and styrene-ethylenebutylene (S-EB), styrene-butadiene (SB) and styrene-isoprene (SI). A preferred diblock copolymer is Kraton® G-1702.

When formed into gels, the hydrocarbon, optionally one or more hydrocarbon-soluble substances, or mixtures thereof, comprises from about 20 to about 95 weight percent of the total weight of the composition. Preferably the total weight of the hydrocarbon, one or more hydrocarbon-soluble substances, or mixtures thereof, contained in the composition will range from about 65 to about 95 weight percent, and more preferably will range from about 80 to about 93 weight percent. Most preferably the total weight of the hydrocarbon, one or more hydrocarbon-soluble substances, or mixtures thereof in the composition of the invention is about 85 weight percent, though this preference may change depending upon the particular application desired, as will be apparent to one skilled in the art.

While not being limited by theory, it is believed that generally the shorter carbon chain length of the hydrocarbon, one or more hydrocarbon-soluble substances, or mixtures thereof, the more volatile is the hydrocarbon. According to the invention, the hydrocarbon, one or more hydrocarbon-soluble substances, or mixtures thereof, is believed to act as a carrier for the active substance in the composition. Thus, when choosing a hydrocarbon, optionally including one or more hydrocarbon-soluble substances, for use in the invention, care must be taken to ensure that the hydrocarbon, or optional one or more hydrocarbon-soluble substances, is of sufficient chain length to become suitably entwined with the polymer blend, such that a desired gel consistency can be obtained for the particular application intended. Under these considerations, volatile hydrocarbon components useful in the practice of the invention are generally preferred to comprise at least about 5 carbon atoms, preferably at least 8 carbon atoms, and less than about 30 carbon atoms, and which may also contain one or more functional groups selected from the group consisting of hydroxyl, carboxylic acid and carboxylic acid esters, and to have a vapor pressure of up to about 600 mm Hg at 20° C. The active ingredients will be released from the gel by evaporation (volatilization). Alternatively, the fragrance(s) and/or deodorant(s) and/or active pest repellent or pesticide may be released by forced air-induced evaporation or by heating.

The hydrocarbons useful in the gels of the invention as defined above include, but are not limited to mineral oils, mineral solvents, mineral spirits, synthetic hydrocarbons (oils and volatile solvents), animal oils, vegetable oils, and mixtures of these hydrocarbons. A preferred group of hydrocarbon oils are synthetic isoparaffin hydrocarbons sold under the trade name Isopar® such as those listed in Table 1, and mixtures thereof.

TABLE 1

| Isopar Product | Approximate Carbon Number |
| --- | --- |
| Isopar C | $C_8$ |
| Isopar E | $C_8$–$C_9$ |
| Isopar G | $C_{10}$ |
| Isopar H | $C_{11}$ |
| Isopar K | $C_{11}$–$C_{12}$ |
| Isopar L | $C_{12}$ |
| Isopar M | $C_{12}$–$C_{14}$ |

The non-aqueous, controlled release air care gels of the invention all incorporate one or more active substances in the gel which is released into the atmosphere or room. These active substances are generally employed in concentrations ranging from about 0.1 to about 30% by weight of the total gel composition. However, it will be recognized by those skilled in the art that active substances can be used up to their characteristic solubility level when so desired.

Useful air care active substances according to the invention comprise, but are not limited to, synthetic deodorizers, natural deodorizers, natural fragrances, synthetic fragrances, synthetic essential oils and natural essential oils. Fragrances may include, but are not limited to, perfumes, essential oils, aroma chemicals, absolutes, balsams, concentrated oils, extracts, infusions, and mixtures thereof. Examples of synthetic and natural fragrances include but are not limited to terpenic hydrocarbons, esters, ethers, alcohols, phenols, ketones, acetals, oximes and derivatives thereof and mixtures thereof. Examples of terpenic hydrocarbons include lime terpene, lemon terpene and limonene dimer.

Examples of the esters include gamma-undecalactone, ethyl methyl phenyl glycidate, allyl caproate, amyl salicylate, amyl benzoate, amyl acetate, benzyl acetate, benzyl benzoate, benzyl salicylate, benzyl propionate, butyl acetate, benzyl butyrate, benzyl phenylacetate, cedryl acetate, citronellyl acetate, citronellyl formate, p-cresyl acetate, 3-t-pentyl-cyclohexyl acetate, cyclohexyl acetate, cis-3-hexenyl acetate, cis-3-hexenyl salicylate, dimethylbenzyl acetate, diethyl phthalate, delta-decalactone dibutyl phthalate, ethyl butyrate, ethyl acetate, ethyl benzoate, fenchyl acetate, geranyl acetate, gamma dodecalactone, methyl dihydrojasmonate, isobornyl acetate, beta-isopropoxyethyl salicylate, linalyl acetate, methyl benzoate, 2-t-butylcyclohexyl acetate, methyl salicylate, ethylene brassylate, ethyl dodecanoate, methyl phenyl acetate, phenylethyl isobutyrate, phenylethylphenyl acetate, phenylethyl acetate, methyl phenyl carbinyl acetate, 3,5,5-trimethylhexyl acetate, terpinyl acetate, triethyl citrate, 4-t-butylcyclohexyl acetate, and vetiver acetate.

Examples of ethers include p-cresyl methyl ether, diphenyl ether, methyl eugenol and phenyl isoamyl ether.

Examples of alcohols include n-octyl alcohol, n-nonyl alcohol, beta-phenylethyldimethyl carbinol, dimethyl benzyl carbinol, carbitol, dihydromyrcenol, dimethyl octanol, hexylene glycol, linalool, leaf alcohol, nerol, phenoxyethanol, 3-phenyl-1-propanol, beta-phenylethyl alcohol, methyl phenyl carbinol, terpineol, tetrahydroalloocimenol, tetrahydrolinalool and 9-decen-1-ol.

Examples of aldehydes include n-nonyl aldehyde, undecylenic aldehyde, methylnonyl ecetaldehyde, anisaldehyde, benzaldehyde, cyclamenaldehyde, 2-hexylhexanal, hexylcinnamic aldehyde, phenyl acetaldehyde, 4-(4-hydroxy-4-methylpentyl)-3-cyclohexene-1-carboxaldehyde, p-t-butyl-a-methylhydrocinnamic aldehyde, hydroxycitronellal, alpha-amylcinnamaldehyde and 3,5-dimethyl-3-cyclohexene-1-carboxaldehyde.

Examples of phenols include eugenol.

Examples of ketones include 1-carvone, alpha-damascone, ionone, 4-t-pentylcyclohexanone, 3-amyl-4-acetoxytetrahydropyran, menthone, methylionone, p-t-amylcyclohexanone and acetyl cedrene.

Examples of acetals include phenylacetaldehyde dimethyl acetal.

Examples of oximes include 5-methyl-3-heptanone oxime.

The active ingredient may also be one or more pest repellents or pesticides. The term "pest" is considered to include any harmful or destructive organisms including insects, nematodes, fungi or the like. Accordingly, the invention is inclusive of all such pest repellents and pesticides, e.g., insecticides, nematocides, and fungicides as well as materials which will repel such pests.

Useful pesticides as an active substance in the invention include N-[[(4-chlorophenyl-)amino]carbonyl]-2,6-difluorobenzamide; 1,1'-(2,2,2-trichloroethylidene) bis(4-chlorobenzene); 2,2-dimethyl-1,3-benzodioxol-4-yl) methylcarbamate; O,O-diethyl-O-6-methyl-2-(1-methylethyl)-4-pyrimidinyl phosphorothioate; and O-ethyl-S-phenyl ethylphosphonodithioate. The pesticides may be of several types; Baits and Stomach Kills including Hydromethylnon (CAS-67485-29-4), Fenoxycarb (CAS-79127-80-3) and Avermectin; Residual Contact Kills such as synthetic Pyrethroids, including Permethrin (CAS-52645-53-1) and Cypermethrin (CAS-66841-24-5), Carbamates including Propoxur (CAS-114-26-1) and Carbaryl (CAS-63-25-2), Phosphorothioates such as Diazinon (CAS-333-41-5) Fumigant Kills including Organophosphates such as DDVP (CAS-62-73-7) and Chlorfeninphas (CAS-470-90-6), Crysanthemums including D-trans Allethrin; and Juvenile Hormones such as Methoprene (CAS-40596-69-8) and Hydroprene (CAS-41096-46-2).

Examples of insect repellents that serve as an active substance in the gels of the invention are N,N-diethyl-m-toluamide, commonly referred to as "DEET," for mosquitos and D-empenthrin for moths, and citronella oil. These insect repellents and insecticides are illustrative of those active substances useful in the practice of the invention. Other active substance insecticides and insect repellents may be suitably used, as is known to those skilled in the art.

In sum, virtually any hydrocarbon-soluble air care active substance known to those skilled in the art may be used in the composition of the present invention. Typically, however, the active substance is one or more high lift, more volatile fragrance, deodorizer, and/or masking agents used in air fresheners and, where possible, should tend to be as non-polar as possible to maximize compatibility with the gel material.

In FIG. 1, the use of three different oils are used with the same formulation to illustrate evaporation rates. Each sample consisted of 91.5 weight percent hydrocarbon solvent, 8.4 weight percent Kraton®G 1650 tribolock copolymer, and 0.1 weight percent Kraton®G 1702 diblock copolymer. Each sample had a surface area of about 3.12 square inches, and was allowed to evaporate at room temperature (ca. 22° C.) over the indicated time period. All three oils were operable but at different rates.

The gels may also contain other additives to change the rate of volatility and/or help solubilize the air care active substance with the gel, for example, surfactants, along with ingredients added to change the physical state of the gel. These ingredients are oil-soluble materials which may stiffen the gel, such as petrolatum, resins, waxes, and materials which may soften the gel or change its rate of release of volatile materials, such as surfactants and oil-soluble liquids such as esters and silicones. A preferred silicone is cyclomethicone, available from Dow Corning. Additionally, antioxidants and other stabilizers may also be present in or added to the gels. Up to 50 weight percent of the hydrocarbon may be replaced by such solubilization substances.

The gel consistency under the invention is controlled by varying the amount, ratio and types of certain polymers, preferably diblock, triblock, radial block and/or multiblock copolymers. The amount of each copolymer and the amount of the mixture contained in the hydrocarbon determines the final form of the gel. In general, the higher the copolymer content, the stiffer the gel. Additionally, the higher amount of triblock, radial block and/or multiblock copolymer in the polymer blend, the stiffer the blend gel. The gels under the present invention range from thin to stiff, as desired, and are generally transparent gels. The polymers under the invention provide gels which have desirable rheological properties and thus provide for novel applications, particularly with respect to non-aqueous active substance air care additives that are sparingly soluble, if at all, in aqueous gels.

Product formation is achieved from block copolymers which will form three-dimensional networks or gels through physical crosslinks. Crosslinking in these block copolymers occurs due to the formation of sub-microscopic particles of a particular block, referred to as domains. Crosslinking of the insoluble domains can be obtained by factors affecting the crosslink density of the networks including length of insoluble block domains, length of soluble block domains, and the number of crosslinkable sites. For example, branched or star polymers and other multiblock copolymers will have more crosslinks than triblock or diblock polymers. The type of solvent or plasticizer to which the blocks are subjected will also affect these characteristics.

Certain gels exhibit syneresis wherein the separation of liquid from the gel by contraction occurs by virtue of the concentration of the insoluble block present in the triblock copolymer. The higher the concentration of the insoluble block, as exemplified by styrene, the more phase separation and crosslinking will occur. However, according to this invention, the amount of syneresis which occurs can be controlled by mixing such systems with diblock, triblock, radial block and/or multiblock copolymers which do not exhibit syneresis.

The composition of the invention has the advantage in that the consistency of the gel can be varied from a semi-rigid gel to a stiff gel depending upon the composition of the polymer blend and, as such, is suitable for uses that cannot be made using particulates and non-self supporting gels. For example, the hydrocarbon gels of the present invention can be used for stand alone air care products, such as air fresheners, having a consistency suitable for stand alone applications.

A further advantage of the air care hydrocarbon gels of the invention is that the gel base is non-aqueous. As such, these gels are more readily useable with non-aqueous active substances including, for example, organic compounds not readily soluble in aqueous controlled-release systems. This increased solubility further permits a greater concentration of many active substances than can be achieved using aqueous gel controlled release systems, thus providing products having stronger fragrance and/or deodorant potentials, when desired. Examples of suitable hydrocarbons include: peanut oils, paraffinic oils and solvents, isoparaffinic oils, naphthenic oils and solvents, natural mineral oils, synthetic oils, synthetic solvents and the like.

In a particularly preferred embodiment of the invention, the gel comprises a blend of a Kraton® triblock copolymer and a Kraton® diblock copolymer, as described herein, in combination with a hydrocarbon, particularly natural or synthetic hydrocarbons which are known as having a smooth homogeneous consistency, and an air care active substance, pest repellent or pesticide. For insect repellent sticks, gels, creams, lotions, etc., the particularly preferred repellent is N,N-diethyl-m-toluamide (DEET). Citronella oil is also a preferred repellent.

It is preferred under the present invention that the end block to ethylene and butylene center block ratio in the triblock copolymer be less than 31:69.

The non-aqueous controlled release air care gels of the invention are prepared by blending into the hydrocarbon one or more triblock, radial block and/or multiblock copolymers, or mixtures thereof, and optionally one or more diblock copolymers, each in the desired amount.

In one method of preparation, the hydrocarbon is first heated to from about 65° C. to about 85° C. One or more triblock, radial block and/or multiblock copolymers, or mixtures thereof, and optionally one or more diblock copolymers, each in the desired amount, is then slowly added to the hot hydrocarbon with agitation. The temperature of the mixture is held for a time sufficient to dissolve the copolymer or blend thereof in the hydrocarbon. Mixing may be carried out in any conventional manner, and is again preferred at this stage. The polymer mix is sufficiently dissolved, generally in about 30 to 60 minutes, when the hydrocarbon/polymer mixture becomes clear and homogeneous. For certain highly volatile hydrocarbons, this mixing may occur in pressure vessels.

The active substance is generally added to the gel in the desired amount at the cooling stage, although in the instance of certain active substances, most notably solid active substances, the addition of the active substance may be advantageously prior to heating the composition to increase the solubility of the active substance. The composition is then poured into a mold or jar and is allowed to further cool to form a gel. Alternatively, if the active substance is particularly volatile, it will generally be added to the composition at a point in the cooling process at which excess premature loss of the active substance is minimized.

In another embodiment of the invention, the hydrocarbon is first heated to from about 65° C. to about 85° C., at which point the copolymer mix is added to the desired weight percent as set forth herein. After sufficient time for the copolymer to melt in the hydrocarbon, the composition is poured into a mold or a jar and is then allowed to cool to form a gel. During cooling, the active substance is generally added. Similar variations of the method of the invention and known to the skilled person in light of the present disclosure are within the scope of the present invention.

Particularly preferred in making the controlled release gels of the invention is to cool the polymer composition in a container or mold, depending upon the final application desired. The container may be any type suitable for the indicated use, as is generally known in the art. As an example of a container, conventional jars, clear, colored or otherwise decorative are also usefully employed for holding non-aqueous, controlled release gels under the invention. A mold is used to impart external features to the final products for those applications were such features are desired in the final product. Additionally, a mold may be used to impart a particularly desired shape into the product. It is also within the scope of the present invention to cool the product in a container directly suitable for end use or compatible with a container suitable for end use.

The non-aqueous, controlled release air care gels of this invention may also contain about 0.01 up to about 5.0 weight percent of one or more conventionally employed additives such as stabilizers, antioxidants, colorants, phophorescing agents and the like to an extent not affecting or decreasing the desired properties of the gel, namely the ability of the controlled-release gel to perform its desired function. With respect to antioxidants, specific reference is made to BHT, which is generally employed at about 0.02 weight percent.

The composition may also be packaged in a conventional aerosol container. Any conventional propellent can be employed. However, for most applications including pesticide sprays, it is preferred to use hydrocarbon gases, dimethyl ether, or R-134a as examples of propellents which do not adversely affect the environment.

Colorants are useful in the invention when desired, as the gel composition is generally transparent. Thus, the gels of the invention can range from completely colorless to having a deep color, as desired, by control of the amount of colorant, if any, employed. The stiff gels may also be multicolored or have colored layers. Other design variations will be readily apparent to those skilled in the art in light of the present disclosure, and are within the scope and spirit of the invention.

The following examples are presented to illustrate the invention, and the invention is not to be considered as limited thereto. In the examples, parts are by weight per 100 weight parts of the composition (i.e. weight percent), unless otherwise indicated.

In these examples, the diblock and triblock polymers used are the preferred Kraton® polymers 1702 and 1650 described above and obtained from Shell Chemical Company. Pennreco 2257 is a hydrocarbon oil with average carbon chain length of about 14 carbons available from Pennzoil Products Company. Geahlene® 1600 comprises a mineral oil and polymer mixture best described by its CFTA definition: "mineral oil (and) hydrogenated butylene/ethylene/styrene copolymer (and) hydrogenated ethylene/propylene/styrene copolymer." Geahlene® 1600 is also available from Pennzoil Products Company.

EXAMPLE 1

In the preparation of a controlled release air freshener gel, the following is prepared:

| | |
|---|---|
| Drakeol ® 7 Mineral Oil | 45.50 |
| Penreco 2257 | 37.00 |
| Polymer 1650 | 16.00 |
| Polymer 1702 | 0.50 |
| Lemon fragrance | 1.00 |

The hydrocarbon mixture is heated to about 75° C., after which the polymers, which have been blended, are slowly sifted in with constant agitation. The temperature is held for approximately 60 minutes to permit the polymer to dissolve in the hydrocarbons, thereby forming a clear homogeneous mix, which is then allowed to cool. As the mixture begins to gel, the active is added with continued mixing. The gel is then allowed to further cool to ambient temperature to result in a stiff, transparent gel suitable for use as an air care product such as an air freshener.

EXAMPLE 2

An air freshener is formed by admixture of the following:

| | |
|---|---|
| Geahlene ® 1600 | 99.00 |
| Lime fragrance | 1.00 |

The Geahlene® is heated to 70° C. and mixed for approximately 45 minutes to obtain a melt. The mixture is allowed to cool, with the active added as the gel begins to form. A soft, clear gel forms upon further cooling and is useful a lime-scented air freshener.

EXAMPLE 3

An air freshener stick is prepared as follows:

| | |
|---|---|
| Isopar L (Isoparaffinic oil) | 37.00 |
| Penreco 2257 | 40.50 |
| Polymer 1650 | 16.00 |
| Polymer 1702 | 0.50 |
| Lemon fragrance | 3.00 |
| Lime fragrance | 3.00 |

The hydrocarbons are first heated and the polymer blend slowly mixed in while maintaining the temperature as in Example 1. As the hydrocarbon/polymer mix cools and gelation begins, the actives are added with continued mixing. The mixture is next transferred to a mold imparting the shape of a stick. After further cooling, a stick-shaped stiff hydrocarbon gel forms which is then encased in a thermoplastic housing suitable for use room deodorizers and air fresheners. The resultant product is useful as a room or car deodorizer and air freshener.

EXAMPLE 4

A room deodorizer is prepared as follows:

| | |
|---|---|
| Active (limonene dimer) | 5.00 |
| Cetearyl Octanoate | 10.00 |
| Cyclomethicone | 5.00 |
| Drakeol ® 7 Mineral Oil | 73.20 |
| Polymer 1650 | 6.45 |
| Polymer 1702 | 0.35 |

The hydrocarbon and polymer are heated as in Example 1, cooled to the beginning of gelation, and the active is added. The resulting product is useful as an air freshener.

EXAMPLE 5

| | |
|---|---|
| Penreco 2257 Oil | 76.50 |
| Kraton 1650 | 15.00 |
| Kraton 1702 | 0.50 |
| Fragrance | 8.00 |

EXAMPLE 6

| | |
|---|---|
| Isopar L | 76.50 |
| Kraton 1650 | 15.00 |
| Kraton 1702 | 0.50 |
| Fragrance | 8.00 |

Examples 5 and 6 are processed as described in Example 1, resulting in products useful as air fresheners.

EXAMPLE 7

Air Freshener Base

| | |
|---|---|
| Isopar L | 80.00 |
| Kraton 1650 | 19.50 |
| Kraton 1702 | 0.50 |

This Example is prepared as in Example 1 with the exception that no fragrance or deodorant is added during preparation. The air freshener base is then heated at a later time and the fragrance and/or deodorant added and the product dispensed into suitable containers or molded into a suitable shape. The product may then be packaged, if desired, and is useful as an air care product.

EXAMPLE 8

| | |
|---|---|
| Isopar M | 63.98 |
| Cyclomethicone (Dow Corning 344) | 15.00 |
| Kraton 1650 | 15.00 |
| Fragrance | 6.00 |
| BHT | 0.02 |

Figure 2:
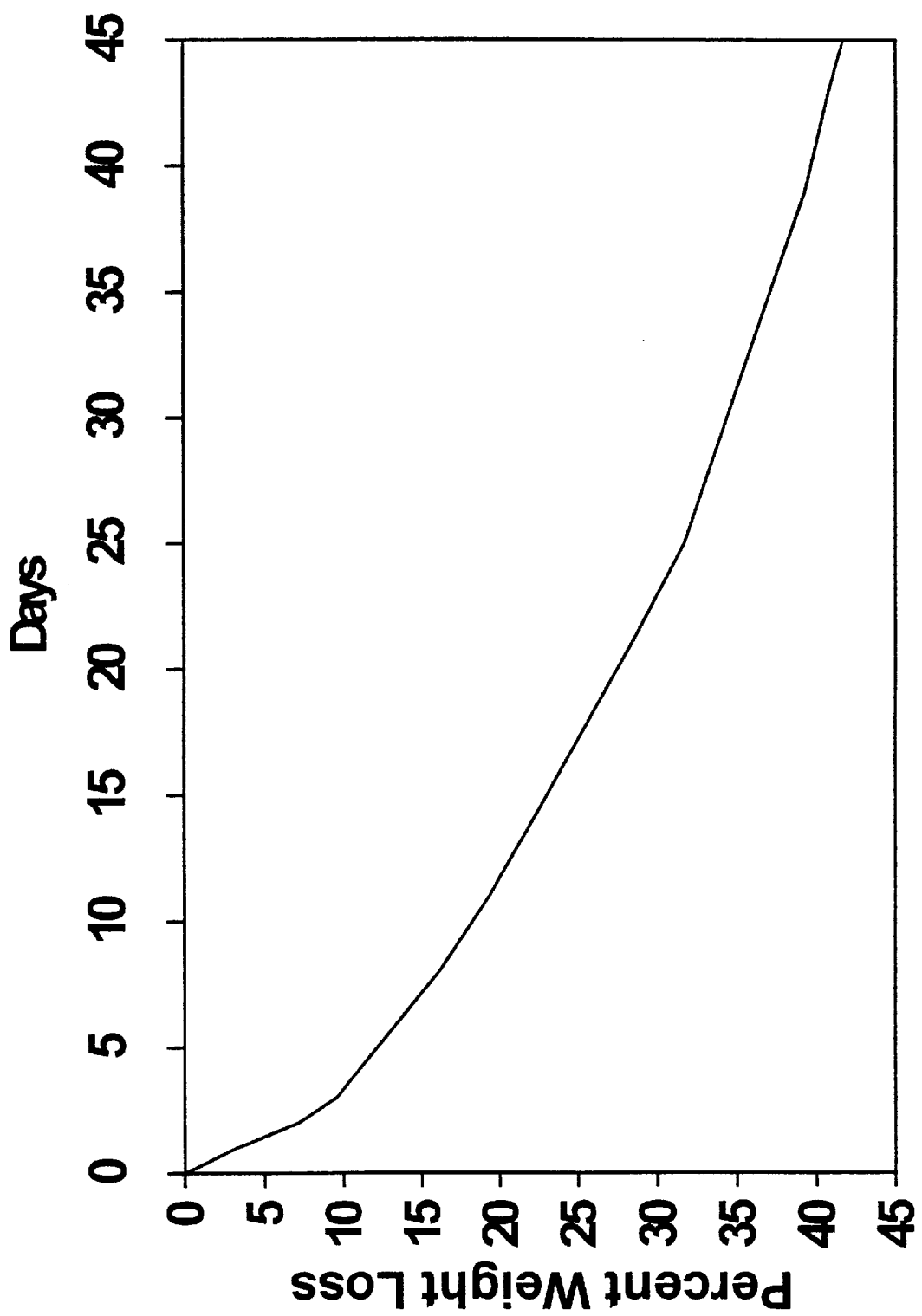
FIG. 2 depicts weight loss of a gel of the invention over time.

The mixture of Example 8 contains a hydrocarbon and hydrocarbon-soluble silicone mix. The mixture is processed as in Example 1, with the fragrance added as the gel cools. The cooling gel was poured into an open round aluminum pan and allowed to solidify at ambient temperature. The surface area of the gel was about 3019 mm$^2$. The mass of the object was periodically recorded and the weight loss noted. FIG. 2 depicts the percent of the weight loss of the gel as a function of time.

EXAMPLE 9

| | |
|---|---|
| Isododecane (Permethyl 99A) | 67.64 |
| Penreco 2251 Oil | 9.80 |
| Kraton 1650 | 9.80 |

-continued

| | |
|---|---|
| Fragrance | 9.80 |
| Isopropyl Myristate | 1.96 |
| Kraton 1702 | 0.98 |
| BHT | 0.02 |

The hydrocarbon mixture is prepared as in Example 1. The resultant stiff gel is useful as an air freshener or deodorizer.

EXAMPLE 10

In the preparation of a controlled release bait insecticide gel, the following was prepared:

| | |
|---|---|
| Drakeol ® 7 Mineral Oil | 45.50 |
| Penreco 2257 | 10.00 |
| Peanut Oil | 27.00 |
| Polymer 1650 | 16.00 |
| Polymer 1702 | 0.50 |
| Hydromethylnon (CAS-67485-29-4) | 1.00 |

The hydrocarbon mixture is heated to about 75° C., after which the polymers, which have been blended, are slowly sifted in with constant agitation. The temperature is held for approximately 60 minutes to permit the polymer to dissolve in the hydrocarbons, thereby forming a clear mix, which is then allowed to cool. As the mixture begins to gel, the active is added with continued mixing. The gel is then allowed to further cool to ambient temperature to result in a stiff gel useful as an insect bait.

EXAMPLE 11

A residual insecticide gel was formed by admixture of the following:

| | |
|---|---|
| Geahlene ® 1600 | 99.00 |
| Permethrin | 1.00 |

The Geahlene® gel is heated to about 70° C. and mixed for approximately 45 min to obtain a melt. The mixture is allowed to cool. Permethrin is then added with mixing as the gel begins to reform, as above. A soft gel forms that is useful as a residual insecticidal composition.

EXAMPLE 12

An insecticidal gel having both volatile actives and residual actives was prepared as follows:

| | |
|---|---|
| Isopar L (isoparaffinic oil) | 37.00 |
| Penreco 2257 | 40.50 |
| Polymer 1650 | 16.00 |
| Polymer 1702 | 0.50 |
| Active-Hydroprene | 5.00 |
| Active-Permethrin | 1.00 |

The hydrocarbons are first heated and the polymer blend slowly mixed in while maintaining the temperature as in Example 10. As the hydrocarbon/polymer mix cools and gelation begins, the actives are added with mixing. Upon complete cooling, a stiff gel forms that is useful as a volatile and surface contact insecticide.

EXAMPLE 13

An insect repellent gel, suitable for application to the skin of a user, was prepared from the following blend:

| | |
|---|---|
| Active-DEET | 10.00 |
| Cetearyl Octanoate | 5.00 |
| Cyclomethicone | 5.00 |
| Drakeol ® 7 Mineral Oil | 73.20 |
| Polymer 1650 | 6.45 |
| Polymer 1702 | 0.35 |

The oil and polymer blend are heated as in Example 10, cooled to the beginning of gelation, and the active substance added. After further cooling, a resultant hydrocarbon gel forms which is an insect repellent gel, suitable for application to the skin of a user.

The invention may also be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. As the invention has been broadly disclosed, the scope of the appended claims is intended to be broadly construed accordingly.

What is claimed is:

1. An article of manufacture comprising a non-aqueous, controlled-release air care composition comprising:
   (a) from about 20 to about 95 weight percent of a volatile hydrocarbon, one or more hydrocarbon-soluble substances, or mixtures thereof;
   (b) from about 1 to about 50 weight percent of a blend of diblock and triblock, radial block and/or multiblock compolymers, said blend comprising from about 0 to about 100 weight percent of one or more diblock copolymer and from about 100 to about 0 weight percent of one or more triblock, radial block and/or multiblock copolymer; and
   (c) from about 0.1 to about 30 weight percent of one or more air care active substances, wherein said one or more active substances are released into the air by evaporation, and wherein said active substances are selected from the group consisting of nematocides and fungicides.

2. The non-aqueous, controlled-release air care composition according to claim 1, wherein said hydrocarbon comprises from about 5 to about 30 carbon atoms.

3. The non-aqueous, controlled release air care composition according to claim 1, additionally comprising one or more solubilizers.

4. The non-aqueous, controlled release air care composition according to claim 3, wherein said solubilizer is a surfactant.

5. The non-aqueous, controlled release air care composition according to claim 1, additionally comprising a stabilizer.

6. The non-aqueous, controlled release air care composition according to claim 5, wherein said stabilizer is an antioxidant.

* * * * *